United States Patent
Kuller

(10) Patent No.: US 10,123,724 B2
(45) Date of Patent: Nov. 13, 2018

(54) BREATH VOLUME MONITORING SYSTEM AND METHOD

(71) Applicant: MYAIR, LLC, Medina, MN (US)

(72) Inventor: David T. Kuller, Milan (IT)

(*) Notice: Subject to any disclaimer, the term of this patent is extended or adjusted under 35 U.S.C. 154(b) by 0 days.

(21) Appl. No.: 15/091,294

(22) Filed: Apr. 5, 2016

(65) Prior Publication Data
US 2016/0213287 A1 Jul. 28, 2016

Related U.S. Application Data

(63) Continuation of application No. PCT/US2015/033703, filed on Jun. 2, 2015.

(60) Provisional application No. 62/007,142, filed on Jun. 3, 2014.

(51) Int. Cl.
*A61B 5/113* (2006.01)
*A61B 5/08* (2006.01)
*A61B 5/091* (2006.01)
*A61B 5/00* (2006.01)

(52) U.S. Cl.
CPC .......... *A61B 5/1135* (2013.01); *A61B 5/0803* (2013.01); *A61B 5/0826* (2013.01); *A61B 5/091* (2013.01); *A61B 5/6823* (2013.01); *A61B 5/7207* (2013.01); *A61B 5/6831* (2013.01); *A61B 5/721* (2013.01); *A61B 2562/0261* (2013.01)

(58) Field of Classification Search
CPC ... A61B 5/1135; A61B 5/0826; A61B 5/7207; A61B 5/6823; A61B 5/091
See application file for complete search history.

(56) References Cited

U.S. PATENT DOCUMENTS

| 4,597,394 | A | * | 7/1986 | Sackner | A61B 5/1135 |
| | | | | | 600/590 |
| 4,715,235 | A | * | 12/1987 | Fukui | G01D 5/16 |
| | | | | | 338/114 |
| 4,807,640 | A | * | 2/1989 | Watson | A61B 5/1135 |
| | | | | | 340/575 |

(Continued)

OTHER PUBLICATIONS

Lukocius et al. "The Respiration Rate Estimation Method based on the Signal Maximums and Minimums Detection and the Signal Amplitude Evaluation." Elektronika ir Elektrotechnika. vol. 88, No. 8 (2008).*

(Continued)

*Primary Examiner* — Meredith Weare
(74) *Attorney, Agent, or Firm* — Winthrop & Weinstine, P.A.

(57) ABSTRACT

A system and method for monitoring the tidal volume of an individual to diagnose a condition is disclosed. The system includes an electrically-conductive, elastomeric band; and a microprocessor having memory. The microprocessor is in electrical communication with said band and has functionality to monitor the respiratory activity of the individual during a period of time, collect raw data from 30 times to 34 times per second, average the data over 9-34 readings, blur from 0.3 seconds to 1.0 seconds of said averaged data to filter out artifacts; determine the beginning of a breath and the end of a breath based on said blurred data; and record an adverse event if a pre-determined period of time has elapsed without a new breath commencing.

17 Claims, 9 Drawing Sheets

(56) References Cited

U.S. PATENT DOCUMENTS

| | | | | |
|---|---|---|---|---|
| 4,815,473 A * | 3/1989 | Watson | ............... | A61B 5/1135 600/534 |
| 4,834,109 A * | 5/1989 | Watson | ............... | A61B 5/0809 600/534 |
| 5,159,935 A * | 11/1992 | Sackner | ............... | A61B 5/1135 600/534 |
| 9,504,410 B2 * | 11/2016 | Gal | ................... | A41D 13/1281 |
| 2002/0032386 A1 * | 3/2002 | Sackner | ............... | A61B 5/0205 600/536 |
| 2003/0187341 A1 * | 10/2003 | Sackner | ............... | A61B 5/0205 600/388 |
| 2004/0143194 A1 * | 7/2004 | Kihara | ................ | A61B 5/1135 600/534 |
| 2007/0293781 A1 * | 12/2007 | Sims | ................... | A61B 5/1135 600/534 |
| 2008/0015454 A1 * | 1/2008 | Gal | ................... | A41D 13/1281 600/509 |
| 2012/0246795 A1 * | 10/2012 | Scheffler | ............... | A41D 1/002 2/69 |

OTHER PUBLICATIONS

International Search Report and Written Opinion issued by the ISA/United States Receiving Office, regarding corresponding patent application Serial No. PCT/US2015/033703, dated Sep. 16, 2015; 8 pages.

* cited by examiner

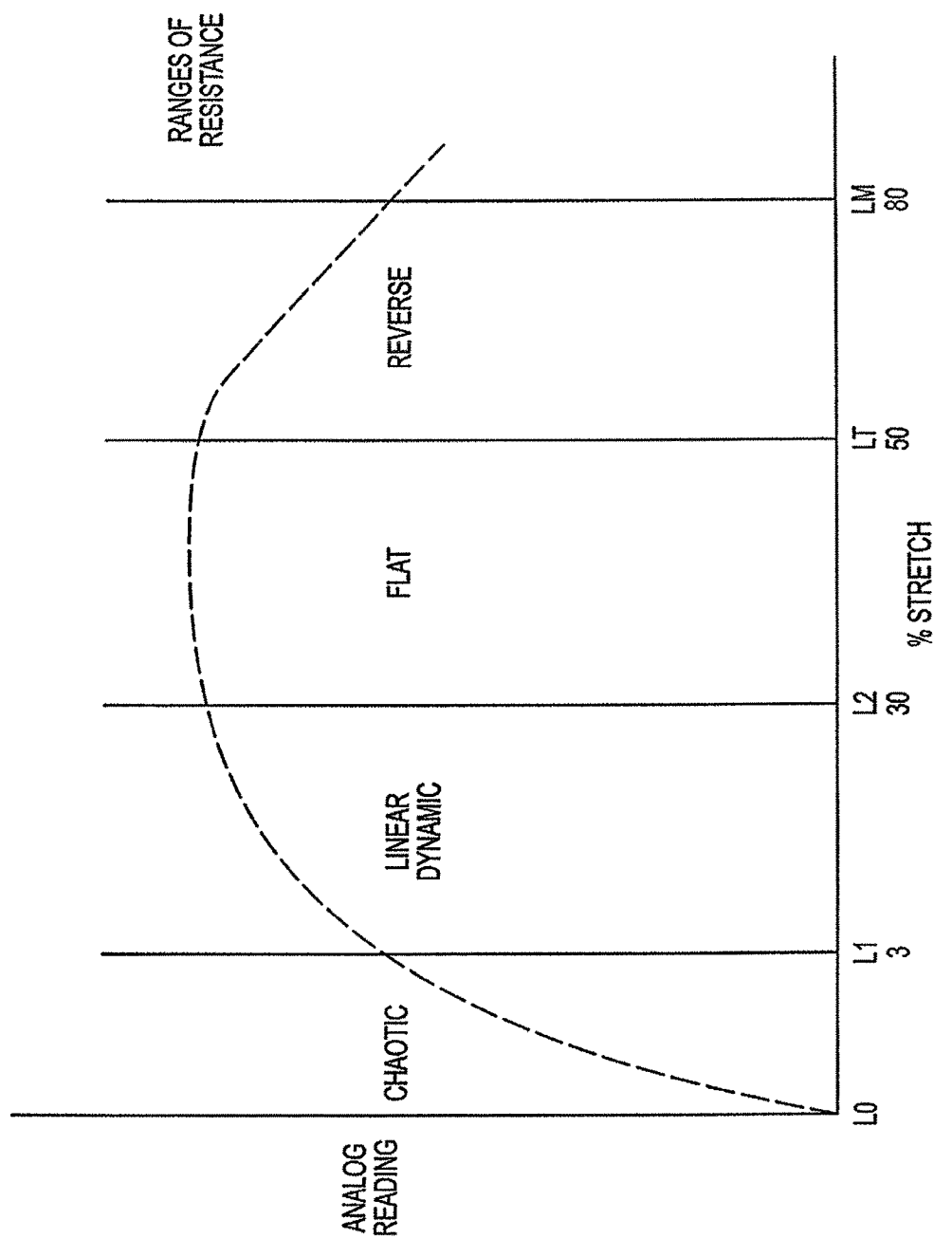

BREATH VOLUME MONITORING SYSTEM AND METHOD

This application claims the benefit of priority under 35 U.S.C. § 365(c) to International Appln. Ser. No.: PCT/US2015/033703, filed on Jun. 2, 2015, which claims priority to U.S. provisional patent application Ser. No. 62/007,142, filed on Jun. 3, 2014, the entireties of which are herein incorporated by reference.

FIELD OF THE INVENTION

The invention relates to a monitoring system for comfortably measuring one or more physiological parameters of an individual. More particularly the invention relates to a system and method that monitors the breath volume of an individual using an electrically conductive elastomeric band.

BACKGROUND OF THE INVENTION

Patients are often treated for diseases and/or conditions associated with a compromised status of the patient, for example a compromised physiologic status. Such conditions may include sleep apnea, which is implicated in atrial fibrillation, hypertension, and chronic fatigue; heart failure, asthma, chronic obstructive pulmonary disease and others. In some instances, a patient may report symptoms that require diagnosis to determine the underlying cause. In such cases, long term monitoring of the patient can provide useful information as to the physiologic status of the patient. In some instances a patient may have been hospitalized and monitoring is necessary in the intensive care unit or post-anesthesia. One example of a device to provide long term monitoring of a patient is the Holter monitor, or ambulatory electrocardiography device, which may use electrodes attached to the skin to measure electrocardiogram signals from the patient.

While effective, Holter monitors are bulky, uncomfortable and do not lend themselves to every application. For example, athletes and other non-patients may want to monitor respiration and/or breath volume for training and conditioning purposes or during competition. Conventional devices, such as the Holter monitor, may not collect all of the kinds of data that would be ideal to diagnose respiration rate or the tidal volume thus making it ineffective for diagnosing and/or treating a patient for apnea. In addition, because a Holter monitor is uncomfortable and bulky, it may result in a "non-compliant" patient or individual because the individual refuses to wear the device and any data that is collected may be incomplete and less than ideal.

Other conventional devices measure physiologic parameters typically by impedance measurements. For example, transthoracic impedance measurements can be used to measure hydration and respiration. Although transthoracic measurements can be useful, such measurements may use electrodes that may be somewhat uncomfortable and/or cumbersome for the individual to wear making long term monitoring more difficult.

Respiratory Inductance Plethysmography (RIP) is a method of evaluating pulmonary ventilation by measuring the movement of the chest and abdominal wall. Accurate measurement of pulmonary ventilation or breathing often requires the use of devices such as masks or mouthpieces coupled to the airway opening. These devices are often both encumbering and invasive, and thus ill-suited for continuous or ambulatory measurements. As an alternative, RIP devices that sense respiratory excursions at the body surface can be used to measure pulmonary ventilation, but are difficult to calibrate and normally only used to measure "effort" not volume. Further, an RIP measurement is reset on every cycle, so no indication of longer term girth size change, drift and/or migration is recorded.

Thus, several sensor methodologies based on this theory have been developed using single elastic bands and dual elastic bands. The elastic transducer bands typically include an embroidered two braided sinusoid wire coils that are insulated by fabric in a lightweight elastic and adhesive band. The transducer bands are placed around the rib cage under the armpits and around the abdomen at the level of the umbilicus (belly button). They are connected to an oscillator and subsequent frequency demodulation electronics to obtain digital waveforms. During inspiration the cross-sectional area of the rib cage and abdomen increases altering the self-inductance of the coils and the frequency of their oscillation, with the increase in cross-sectional area proportional to lung volumes. The electronics convert this change in frequency to a digital respiration waveform where the amplitude of the waveform is proportional to the inspired breath volume. However, this methodology requires expensive electronics and essentially passes radio waves through the body which may prove deleterious to an individual's health.

RIP technology has been incorporated into stretch garments and bands but the state of the art in resistive stretch sensors is not ideal. Typically the resistance increases for a certain percentage of stretch up to a point then decreases with increasing stretch. In other words, there is not a good 1:1 correlation between stretch length and resistance. Further the resistance is temporarily affected by the change in length and the speed of that change resulting in situations in which the resistance actually increases when the material recovers to shorter lengths after being stretched. Moreover, knitted, stretch fabrics are extremely variable as are the electrical characteristics of knitted fabrics with conductive/resistive threads. Further, motion artifact affects accurate measurements with changes in resistance tied to motion and length.

Thus, known methods and devices for long term monitoring of individuals may be less than ideal. At least some of the known devices may not collect the right kinds of data to treat patients optimally and are not readily available to athletes and other individuals who want to use the devices for non-medical reasons such as for training purposes.

Therefore, a need exists for an improved, comfortable, continuous, ambulatory monitoring system and method that is capable of providing accurate respiratory volumetric dynamics data and that overcomes the short-comings of conventional methods and devices.

BRIEF SUMMARY OF THE INVENTION

The foregoing needs are addressed by the system and method for monitoring respiration rate and volumetric dynamics in accordance with the invention.

In one aspect of the invention a stretchable, knitted matrix of nylon, spandex and silver wires is provided.

In another aspect of the invention, direct current is used as opposed to alternating current which substantially reduces the issues with radio signals being passed through the body.

In one aspect of the invention, the system provides real-time, non-invasive measurement of breath volume dynamics with remote monitoring that provides total comfort for a patient and other individuals.

In another aspect of the invention, the system takes the form of an elastomeric chest band that encircles the lower chest and floating ribs of a patient or individual.

In another aspect of the invention the elastomeric chest band comprises knitted silver coated nylon yarn.

In a further aspect of the invention, the chest band wirelessly communicates with a computational device.

In another aspect of the invention, the system calculates resistance continuously.

In another aspect of the invention, the resistance changes with each expansion and contraction of the chest band while expansion occurs with inhalation and contraction occurs with exhalation.

In another aspect of the invention the system is useful with a plurality of patient conditions such as assessment for obstructive sleep apnea and sleep hypopnea syndromes, Cheyne Stokes, gasping for breath and other sleep-related breathing disorders; the transition from sleep to wakefulness such as in post-anesthesia recovery; maintenance of wakefulness such as in postoperative monitoring or monitoring when sedating medications (narcotics) are being use; transition from illness to health such as incentive spirometry to promote lung recruitment and restoration of baseline pulmonary function; promotion of health such as measuring respiratory activity as part of the quest for personal fitness and a healthy lifestyle; and maximization of health such as fitness training and elite athletic performance.

In another aspect of the invention, the system provides real time feedback to other medical devices to improve their performance both in terms of real time use and after the fact analysis. By way of example the system may be used to activate or modify the pressure of a continuous positive airway pressure device (used to treat apnea) in real time according to the current state of the patient's breathing patterns.

The system in accordance with the invention monitors the tidal volume of an individual to diagnose a condition and includes an electrically-conductive, elastomeric band; a microprocessor having memory, the microprocessor in communication with the band and having functionality to monitor the respiratory activity of the individual during a period of time, collect raw data from 30 times to 34 times per second, average said data over 9-34 readings, blur the averaged data from 0.3 seconds to 1.0 seconds to filter out artifacts; determine the beginning of a breath and the end of a breath based on said blurred data; and record an adverse event if a pre-determined period of time has elapsed without a new breath commencing.

The method in accordance with the invention monitors the tidal volume of an individual to diagnose a condition and includes providing an electrically-conductive, elastomeric band in communication with a microprocessor having memory; monitoring the respiratory activity of the individual during a period of time by causing the microprocessor to collect raw data from 30 times to 34 times per second; averaging the data over 9-34 readings by the microprocessor; blurring the last 0.3 to 1.0 seconds of the averaged data to filter out artifacts; determining the beginning of a breath and the end of a breath based on the blurred data; and recording an adverse event if a pre-determined period of time has elapsed without a new breath commencing.

While multiple embodiments, objects, features and advantages are disclosed, still other embodiments of the invention will become apparent to those of ordinary skill in the art from the following detailed description taken together with the accompanying figures, the foregoing being illustrative and not restrictive.

BRIEF DESCRIPTION OF THE DRAWINGS

For a better understanding of the invention, and to show how the same may be carried into effect, reference will now be made, by way of example, to the accompanying drawings, in which:

FIG. 3 is an exemplary graph showing the non-linear resistance/stretch curves of the resistive fabric that is used in the system in accordance with the invention.

DETAILED DESCRIPTION OF THE INVENTION

Unless defined otherwise, all technical and scientific terms used herein have the same meaning as is commonly understood by one of skill in the art to which this invention belongs.

As used herein, the following terms have the ascribed meaning.

Tidal volume (Vte) is the volume inhaled with each breath. Variability in the wave form can be used to differentiate between restrictive (less) and obstructive pulmonary diseases.

Minute ventilation or volume is equivalent to tidal volume multiplied by respiratory rate and is used to assess metabolic activity. However, minute ventilation/volume multiplied by respiratory rate is often an inaccurate approximation in the presence of irregular breathing. Another way to calculate Minute Volume is to add together a sequence of breath's Tidal Volumes over a one minute period of time or any other period of time normalized to a minute.

Figure 1:
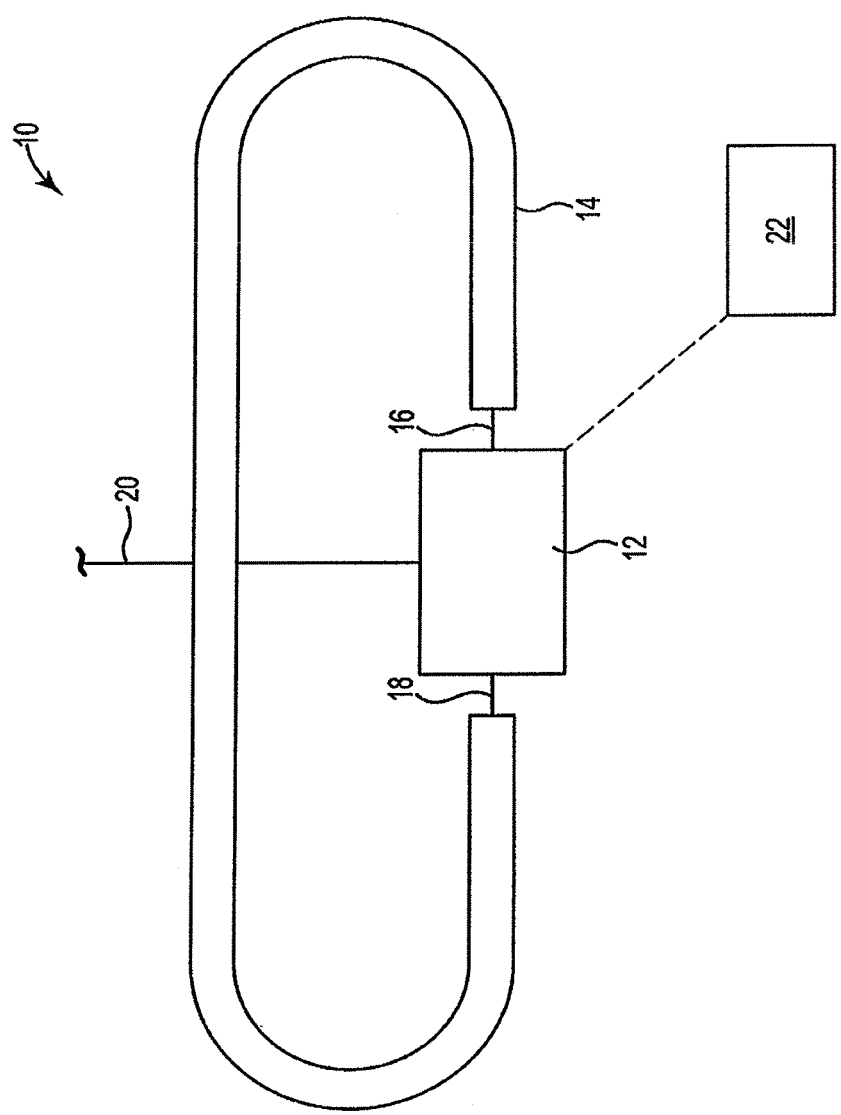
FIG. 1 is a perspective view of the system in accordance with the invention depicting the components of the system.
Figure 2A:
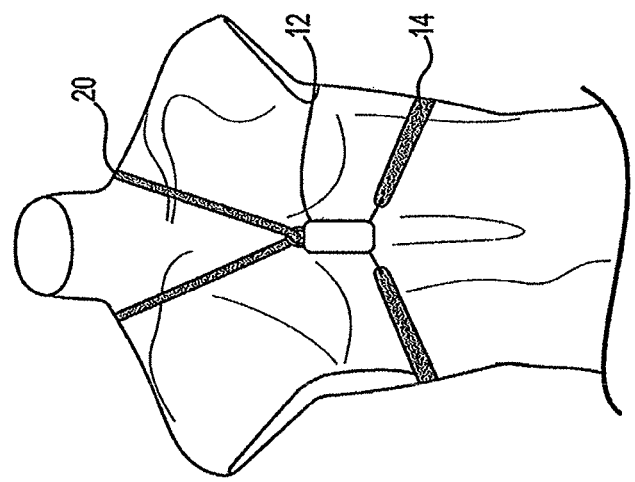
FIGS. 2A, 2B and 2C are illustrative views depicting the single belt fit afforded by the elasticity of the system in accordance with the invention.
Figure 2B:
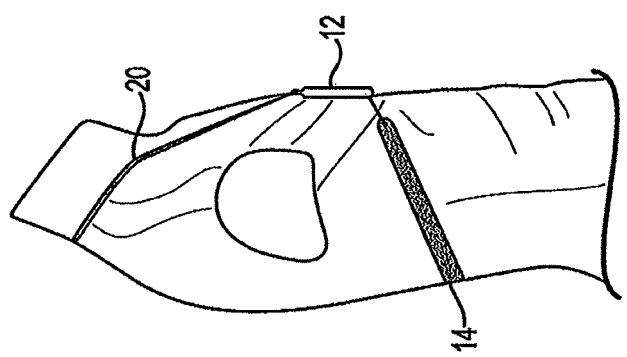
Figure 2C:
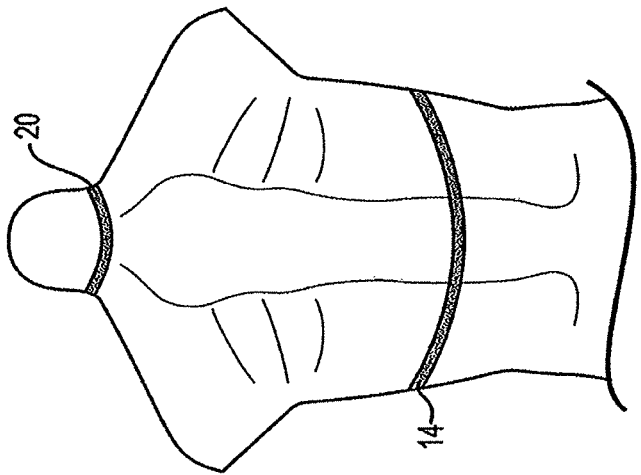

Referring now to the Figures, the invention will now be described in detail. FIG. 1 depicts various components of the system in accordance with the invention. The invention 10 includes a microprocessor 12 operably coupled to a knitted silver, conductive/resistive, elastic thoracic girth band 14. Microprocessor 12 includes an analog to digital converter that converts the spontaneous resistance level of the girth band 14 into a 10 bit number thus generating "raw sensor data." Microprocessor 12 generates Tidal Volume information based on the change in girth band resistance over time to determine Minute Volume data, which is used in determining adverse breathing events. Microprocessor 12 may also include rechargeable Bluetooth and wireless capabilities and means to store an SD card to capture data. The girth band 14 is coupled to the microprocessor 12 by electrical connection 16 and ground 18. Microprocessor 12 is anchored to the individual by attachment means 20. As depicted in FIGS. 2A, 2B and 2C attachment means 20 is an elastic necklace, however those of skill in the art will appreciate that attachment means 20 may comprise a clip, necklace, pin or other such attachment means known to those of skill in the art. Microprocessor 12 includes a rechargeable battery for operating the microprocessor 12 and for charging the band 14, communication means such as Bluetooth for communication with computational means 22 and an algorithm that measures the volume of breath by taking continuous measurements of lower ribcage girth dynamics and records and outputs data on start of breath to peak of breath as well as the raw sensor data. Computational means 22 may be a laptop computer or other such computational elements known to those of skill in the art. Microprocessor 12 may be further connected to an onboard storage device such an SD memory card, for recording breathing data in the absence of a wireless connection. Thus, the data collected may later be easily transferred to a computer for analysis. The device's onboard microprocessor is also equipped with a motion detection circuit, for example a nine axis motion detector consisting of a three axis accelerometer, a three axis rotation sensor and a three axis magnetic field sensor. The motion detection circuit provides movement and postural orientation data points to augment the breathing information in the context of the patient's posture and movements.

FIG. 2 depicts the unique single belt fit afforded by the elasticity of the girth band 14 used with the system in accordance with the invention. The girth band 14 is anchored to the individual by attachment means 20. The girth band 14 is operably coupled at a first end to the microprocessor 12 and then encircles the torso at the lowest rib. It then couples at a second end to the microprocessor with second attachment means. In use the girth band 14 is pre-tensioned to ensure a fit around the torso that will not dislocate the band 14 during, for example, sleep. Advantageously, this unique fit allows the invention to continuously record data without interruption. The inventor has found that the human torso's circumference reduces significantly during the sleep process requiring that the girth band 14 be pre-tensioned enough to overcome the physiological reduction in size without loosening while in position during the sleep cycle. For the comfort of the patient, it is fundamental that this pre-tensioning does not create discomfort by being too tight, which requires extreme elasticity in the strip material. When properly fitted the girth band 14 may be used directly against the skin, over a layer of clothing or between layers of clothing.

FIG. 3 shows a typical stretch metallic knit "static" resistance curve. Initially, the resistance change with elongation rapidly changes (L0 to L1). Following the initial phase, there is a linear increase in resistance with respect to length (L1 to L2). Resistance continues to increase with length but in decreasing increments as shown from L3 to Lt or length threshold. Above the length threshold, resistance decreases with increasing length until the elastic band reaches its maximum length (Lm). From the foregoing we can see that the operative useful range of the band is within the range of L1-L2 in order to achieve accurate calculations without significant calibration difficulties.

Figure 4:
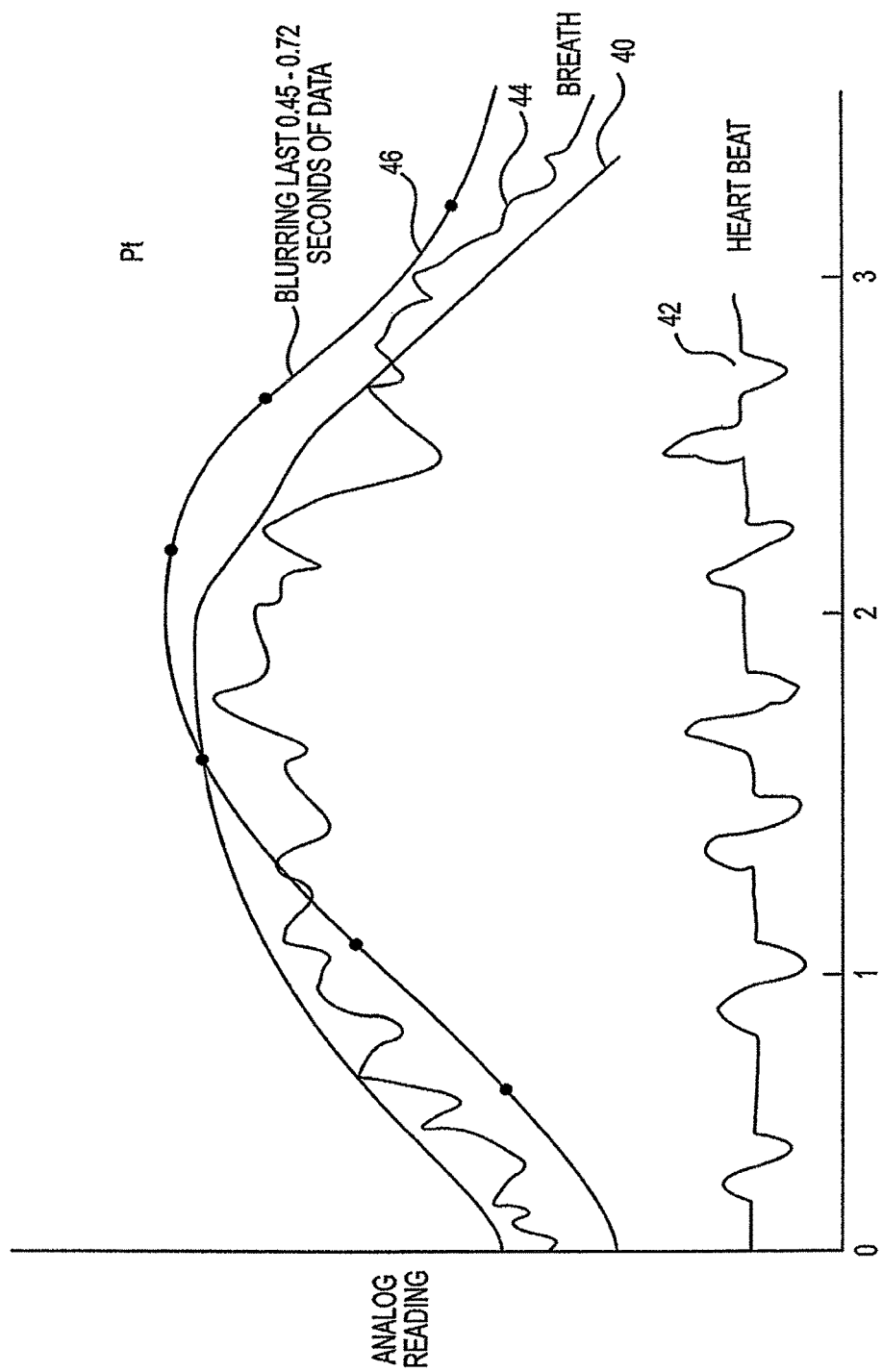
FIG. 4 depicts the parametric blur of heartbeat and other non-breath body motion.

FIG. 4 depicts how the physical girth measurement is in part tied to the heartbeat and other body motions, not just the breathing cycle, which is far slower. It also shows how by averaging out from 0.3 to 1.0 seconds worth of girth readings, the heartbeat can be "smoothed" out and stop producing troughs and peaks that are not related to breath. Lower blur times, i.e. 0.3 to 0.5 afford measuring faster breathing rates as with babies and small animals. A higher blur time, i.e. 0.6 to 1.0 afford a better distinction between big heart throbs/beats and small breaths. For sleep related disorders a blur time of from 0.5 to 0.8 and preferably 0.72 provides accurate measurements. More specifically this graph illustrates the following:

girth related to breath (smooth bell shaped curve) (40)
girth related to heartbeat (heart beat line) (42)
total girth unfiltered (bell curve with peaks and troughs) (44)
total girth "blurred" by 0.72 seconds (46)

When a deflection downward in the smoothed curve is detected, the trough and peak of the previous breath are chosen from the raw data points encountered since the end of the previous breath cycle. When the trough and peak are derived from the smoothed data, the risk is a flattening of the data, reporting reduced tidal volume compared to the actual breath size.

Figure 5:
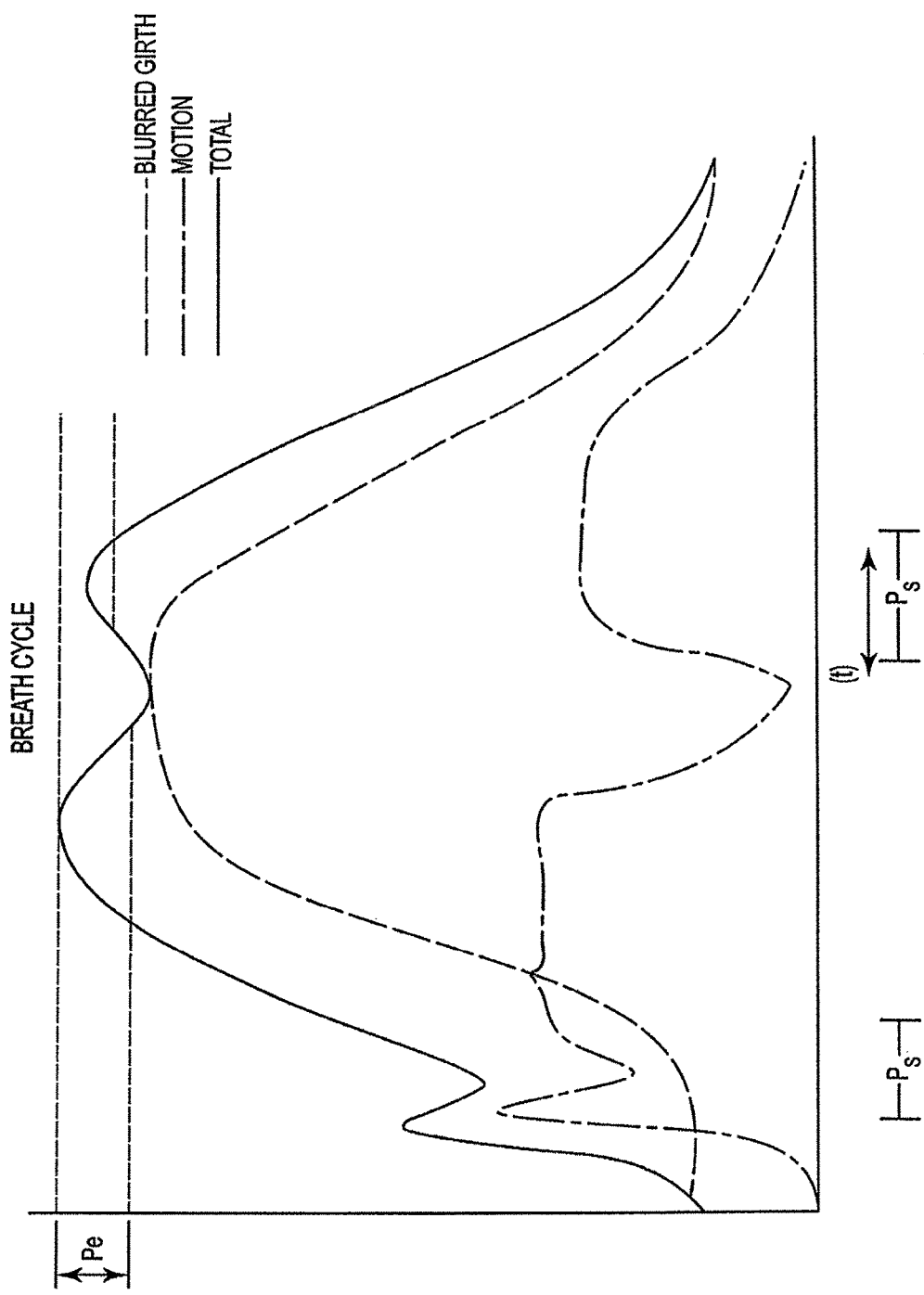
FIG. 5 depicts knit motion artifact filter parameters Pe and Ps.

Referring now to FIG. 5 knit motion artifact filter parameters are shown. This graph illustrates the actual resistance readings from the band used in the system in accordance with the invention. The total measured breath cycle resembles an upside down W contrary to what a normal breath bell curve should look like. This "non-correspondence" is due not only to the heartbeat and the smoothing (Pt) done by the algorithm but also because of motion and acceleration artifacts inherent in the knitted metallic band. In other words, a portion of the resistance is "static" and is related to the static length of the stretched knit (the overall bell shape), but much of the resistance is also due to the spontaneous motion of the fabric—it is higher when stretching or recovering, more so the faster the acceleration. This accounts for the slight "hump" at the beginning of the total measured breath cycle as depicted, and the double "hump" in the middle. Referring to FIG. 6B, the breath cycle is measured at point Pi (to detect new breath), Pe (to detect end of breath) and Ps (to detect false short breaths). Therefore, as those of skill in the art will appreciate, the upside down W of FIG. 5 is related to the speeding up and slowing down that happens twice in every breath at the girth. The sensor's data is first filtered with a subsampling/averaging/blurring of four data points to significantly reduce the high frequency and high amplitude of the heartbeat components in the calculation of Tidal Volume.

Figure 6A:
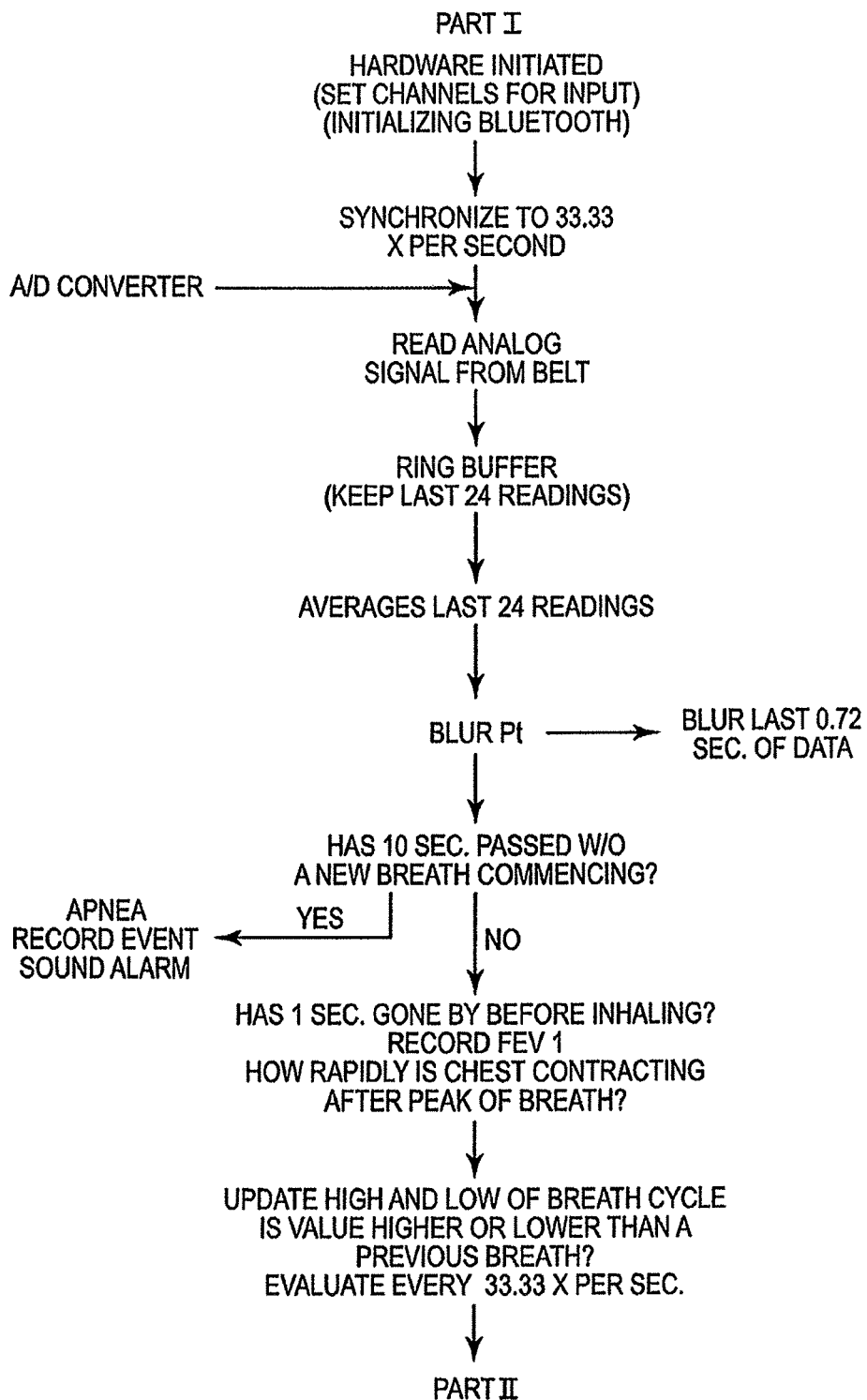
FIG. 6A-6B are flowcharts depicting the onboard breath dynamics monitoring and logic flow chart of the system in accordance with the invention.
Figure 6B:
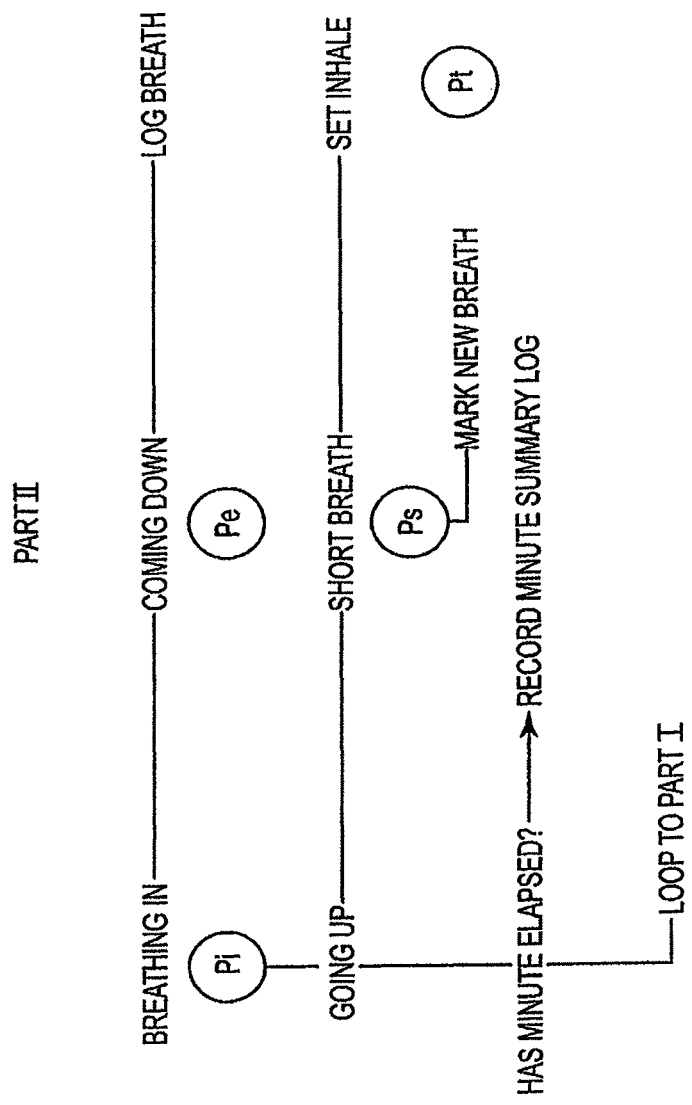
Figure 7A:
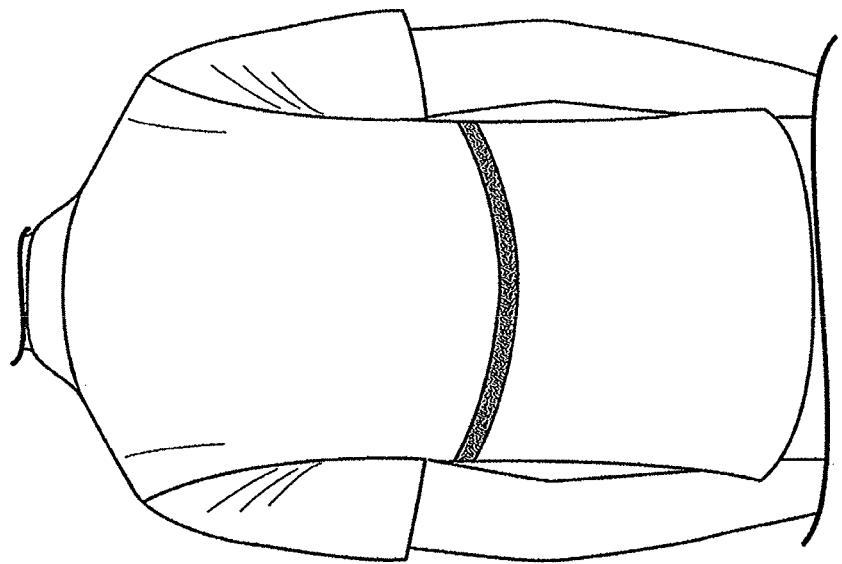
FIGS. 7A-7B illustrate the girth band in accordance with the invention positioned over the clothing of an individual user.
Figure 7B:
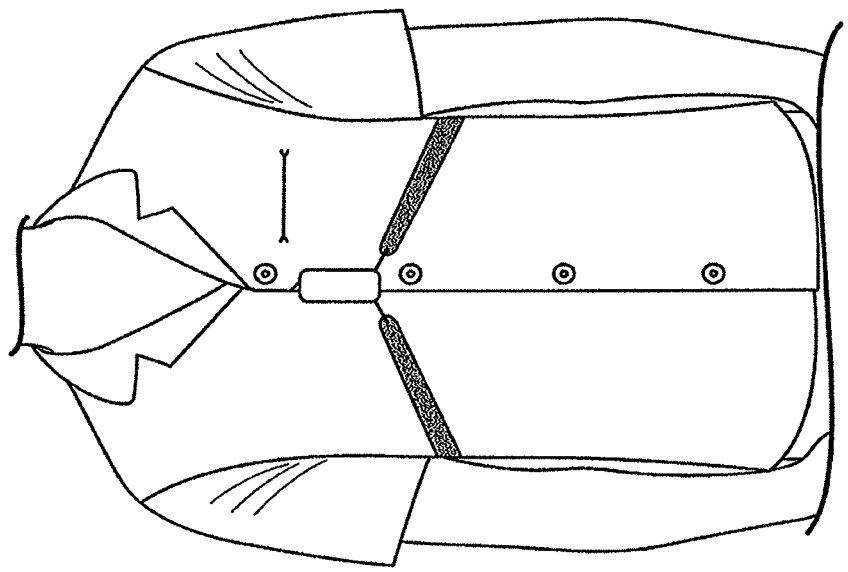

Referring now to FIG. 6A-6B, flowcharts of onboard breath dynamics monitoring are depicted. The flowcharts depict how first the raw data is smoothed over time to filter out the heartbeat. It then shows how beginning and end of breaths are measured, and how short breaths are removed. It also depicts how minute data are inserted into the stream.

Thus, the objective of the data stream analysis depicted in FIG. 6A-6B is to on a breath by breath basis over a continuous time period, time stamp the beginning and ending points of each breath and their associated girth dimensions then calculate from this the volume of each breath. The resulting information is wirelessly transmitted to computational means such as a laptop or other computer and/or saved to the onboard SD card.

Other time stamped data including Fev1 (forced evacuation volume after 1 second) are further extracted from the sensor data stream and included in the wireless log. Periodic time summary data is also included in the stream regarding the last minute's breathing. The stream is encoded in a format to distinguish breath by breath data from periodic time summary data. Time stamped raw sensor data and smoothed data are also encoded into the data stream.

It is not a simple matter of looking at the "raw" data coming from the A/D converters both because of the non-linear behavior of knitted sensors and because of the plethora of other body articulations unrelated to breathing that nonetheless affect the lower chest girth size measurements. For example, the band in accordance with the invention is sensitive enough to capture the changes in chest size related to the simple beating of the heart. Many movements involving posture or the use of arms and legs can significantly change the shape of an individual's chest and related girth size.

The detection of inhale/exhale moments in the data stream is not simply a matter of when the input values go up and down. Those of skill in the art will appreciate that many other factors not related to the breath cycle may influence the stretched length of the band in accordance with the invention, causing girth measurement inflections at a much higher frequency than that of the breath.

The algorithm used in the system in accordance with the invention is capable of parsing breath related data inflections because other types of bodily movements such as heartbeat, arm movements, and the like creates band resistance waveforms outside of the time domain of the breath cycle, hence they can be filtered out leaving a good approximation of the breath dynamics.

A filtering algorithm is used to remove motion artifact inherent in knitted metals within the limited scope/domain of the breath cycle and simultaneously enhance limited bit analog to digital converters found in less expensive microprocessors. Further data analysis is done to eliminate other bodily movements not related to the breath cycle, including heart beats, simple movement.

A discussion of parametric (Pt, Pi, Pe, Ps) extraction of breath inflection points follows. Raw data is first input 30 to 34 per second through a 10 bit analog to digital converter. The data are kept in a first in, first out buffer to facilitate calculation of averages. For purposes of breath detection, the absolute data is averaged over the past 20-30 readings and optimally at least 24 readings, a minimum of from 0.45 to 0.72 seconds (Pt)—the equivalent of having approximately 5 bits more accuracy. By averaging over such a long period, the momentary vibrations of the band due to body motion and heart beat are filtered out. Those of skill in the art will appreciate, however, that the combination of parameters of breath measurements evaluated every 30 to 34 times per second; averaging the past 20-30 readings and preferably 24 readings; and blurring the last 0.45 to 0.72 seconds of data is optimized for breath and heart dynamics during the sleep cycle to diagnose sleep disorders. The 0.45 to 0.72 second of blur substantially eliminates heartbeat related higher frequency "noise." The blur is used to detect macroscopic lower frequency but higher magnitude inflection in the input stream—then use the non-blurred data for more precision in the Tidal Volume calculation.

For diagnosing and treating other abnormalities the frequency of measurement may be 100 to 1000 times per second because much more detailed information may be seen at higher frequency pulsations (from 50 Hz to 500 Hz). The higher frequency sample rate is useful for "phonocardiogram" analysis of the heart. Lower frequencies are useful in analyzing breathing disorders. For example, in making a determination of an hypopnea event the microprocessor measures a large cluster of breaths and uses them as a "reference." The microprocessor then measures smaller clusters of breaths and measures decreased breathing. The user can select how many breaths to consider as reference, and how many breaths to look at for measuring temporary drops. The inventor has found that twenty breaths provides a stable reference but moves smoothly with the bodies metabolism over time. Similarly three breath clusters are used to detect drops in breathing—when a small cluster dips below the hypopnea threshold. If breath measurement falls below the threshold for at least 10 seconds a hypopnea event is noted. This approach, i.e. the normalized small cluster divided by the normalized reference cluster, approximates blood oxygen desaturation and also predicts a series of related sleep disorders, including hypopnea and respiratory related arousals. The system in accordance with the invention measures decreased breathing. In other words, the system in accordance with the invention measures the cause of reduced breathing (reduced Vte and Minute Volume) as opposed to the effects of reduced breathing which conventional devices measure using PSG (polysomnogram) data.

When a user or a clinician is analyzing sleep (or active wakefulness data) a viewing span (start time and total viewing time) is chosen and the software used with the system in accordance with the invention automatically "counts" semaphore data and reports the number of apnea, hypopnea, and jumps in the given period, as well as a "total time in hypopnea" and "percent of the period in hypopnea"—all parameters that are useful for assessing the quality of the sleep in that period and useful in diagnosing sleep or other disorders.

The software continuously determines a first inhale followed by an exhale. This allows for the determination of the size of each breath and their tabulation and inclusion in minute data calculations. But the girth data is ultra-sensitive to many body motions and internal organ movement, including the heart. So it is vibrating at many different frequencies and amplitudes. Furthermore, the girth data is related to both the stretch length and the stretch motion and velocity. It is not a simple question of measuring the troughs of each inflection in the input data stream.

The algorithm used in the software in accordance with the invention determines the beginning of a breath when the averaged input increases from the lowest recent trough by at least the equivalent of +0.1 (Pi) on a scale of 100 (max breath). That is a $1/1000^{th}$ degree of sensitivity. Note that this is a 10 bit sensitivity despite the fact that the input stream varies by 7 bits at most between min/max girth. The extra bits of data accuracy arise from the time averaging (Pt).

The ending of a breath is determined by the computational means when the girth is either smaller than what it was when the breath began or when the girth is smaller than the maximum girth in this breath cycle minus 0.05 (Pe). This value best eliminates the motion artifact inherent in the data stream related to the inventive band as pertaining to inhale/exhale muscular inflections and knit dynamics. Without this filter, many otherwise smooth breaths would get counted as a series of smaller back to back breaths because of fluctuations due to the motion and velocity artifact. This filter opens a wider range of breath speeds that the software can accurately detect despite motion/velocity artifact. Furthermore this filter helps correct for situations when a rapid exhale would otherwise be seen as an extra breath (because of the exaggerated motion artifact from the speed of the exhale that would be intense enough to register as a new incoming breath).

If the "sensed" end of the breath is detected before the minimum breath length of 0.1 second (Ps) as compared to the time stamp of the beginning of the breath, it is rejected and the original breath state returns to "inhaling looking for exhale" recovering the previous beginning point. This effectively removes many of the false new breaths that would otherwise be associated with the motion artifacts in the original data stream. It implies a maximum accurate breath rate of 5 breaths per second. The algorithm then begins looking for the beginning of a new breath.

Fine tuning of the P values ensures that the bands are comfortable throughout the fit range and able to accurately measure from the smallest breaths in reclined deep sleep to the largest breaths in upright activity, minimizing body articulation and heart beat interference to breath measurement.

The algorithm is more likely to report "extra" breaths in extreme ventilation/movement conditions but as a result is far more accurate with the smaller breaths associated with more critical moments of apnea. This compromise was chosen because as a diagnostic tool we are more interested in the apnea end of the spectrum than in the extreme sport area. The over reporting of breaths is well within the accepted standards of performance in prior technology spirometers which are far more invasive. Some types of heartbeats and restricted upper airway breathing can cause this algorithm to break up longer, deeper breaths into a sequence of smaller but progressive breaths. This leads to roughly the same Minute volume calculation but indicates a higher breath rate. When properly visualized these smaller progressive breaths indicate to the diagnostician the type of heart/obstructive breathing which is useful for understanding the patient's pathology.

The algorithm may also skip the counting of some breaths in situations of hyperventilation exceeding 2 breaths per second.

To record quality results using the system in accordance with the invention, the band needs to be properly fitted. To overcome the first chaotic range of resistance (L0-L1), the band is clipped approximately 7% (Fp) shorter than the actual girth, for example 4 cm out of 60 cm. The system calculates data so long as the band is comfortable despite being pre-stretched to L1, and remains comfortable up to 25% larger chest expansion (15% for size change during day, 10% for max breath). This calls for an operational range of at least 28%. So long as the L2 of the supplied band is at least +28% of L0, then the algorithm will correctly analyze results. Pre-tensioning eats up the L1, full breath dynamics range of 25% in the L1-L2 range with quick recoil and comfort.

Math takes advantage of cylindrical approximation of chest cavity where delta girth is linearly related to delta volume of cylinder. So if the resistance curve of the elastomeric girth band is in the L1-L2 range, it is roughly linear and the volumetric approximations will be accurate.

Typically girth based breath dynamic systems (RIP) have used fairly tight belts placed around various sections of the rib cage, from just under the armpits, over the nipples, across abdomen (accepted terminology). One of the problems noted is the sliding of the belts position, sliding up/down during tests altering measurement accuracy. The tendency is to tighten the belts to get them to hold their place, leading to less comfort. It would seem like these fit points were chosen more as a question of clear reference points (arm pits, nipples) than in terms of usefulness towards the objective of lung volume calculations.

Contrary to the foregoing, the band in accordance with the invention clips the computational means onto the patients clothing just over the chest plate area such that the connection points for the band ends are just above the bottom of the sternum. The band is then connected first to one side of the computational means, then is led around the thorax in such a way that is follows the groove just above the lowest rib of the lower ribcage (starting higher in front, sashing lower in back). Starting first with an un-stretched band the length of the foregoing circumference, it is then shortened by approximately 3 cm and clipped to the other lead of the sternum mounted computational means. In order to determine the patient's minimum girth, a pre-fitting technique has been developed wherein the patient is asked to stand up and bow his head downward, curving his back, pushing the lower ribs down and back while exhaling as much as possible. In this position, a tape measure is drawn tight around the lower ribs from the sternum to determine the patient's minimum girth. This length is further reduced by 4 cm and even further reduced by the clip to clip distance of the electrical connection points of the microprocessor. The strip is then cut to this final length.

The girth size thus measured is a "best compromise" for measuring three different types of breaths—intercostal, diaphragmatic, mixed intercostal/diaphragmatic. All three types of breaths have a significant impact on this measurement unlike any other circumference point (i.e. armpit, nipple, abdomen). The combination of the elasticity of the band in accordance with the invention and the sternum mounting point of the computational means and the pre-tensioning leads to a good balance between comfort, accuracy, and consistency of placement against slippage right at this fitting point (i.e. just above lowest rib). This lower rib fitting point has proven to work on all sizes and shapes of humans from newborns to extremely obese adults. This fitting point is also consistent on other mammals such as dogs, cats, horses and the like.

Before using the system in accordance with the invention with sleep tests, the band should be pre-tensioned only after the patient has expelled as much air as possible simulating how they will get smaller during sleep. The reason this fit leads to accurate measurement has to do with how these lowest ribs move both when intercostal breathing occurs (dragged along by their connection to upper rib movement) and during pure diaphragmatic breathing caused by the natural reaction of abdominal muscles to push the organs up into place and force the lower floating ribs to expand to take in the air, and not the organs displacement downward. This use of the abdominal muscles to push back against diaphragm movement is a natural and instinctive behavior and occurs naturally even as you sleep. So despite not using intercostal muscles, the lower ribs nonetheless expand proportionally with diaphragmatic breathing.

Figure 8:
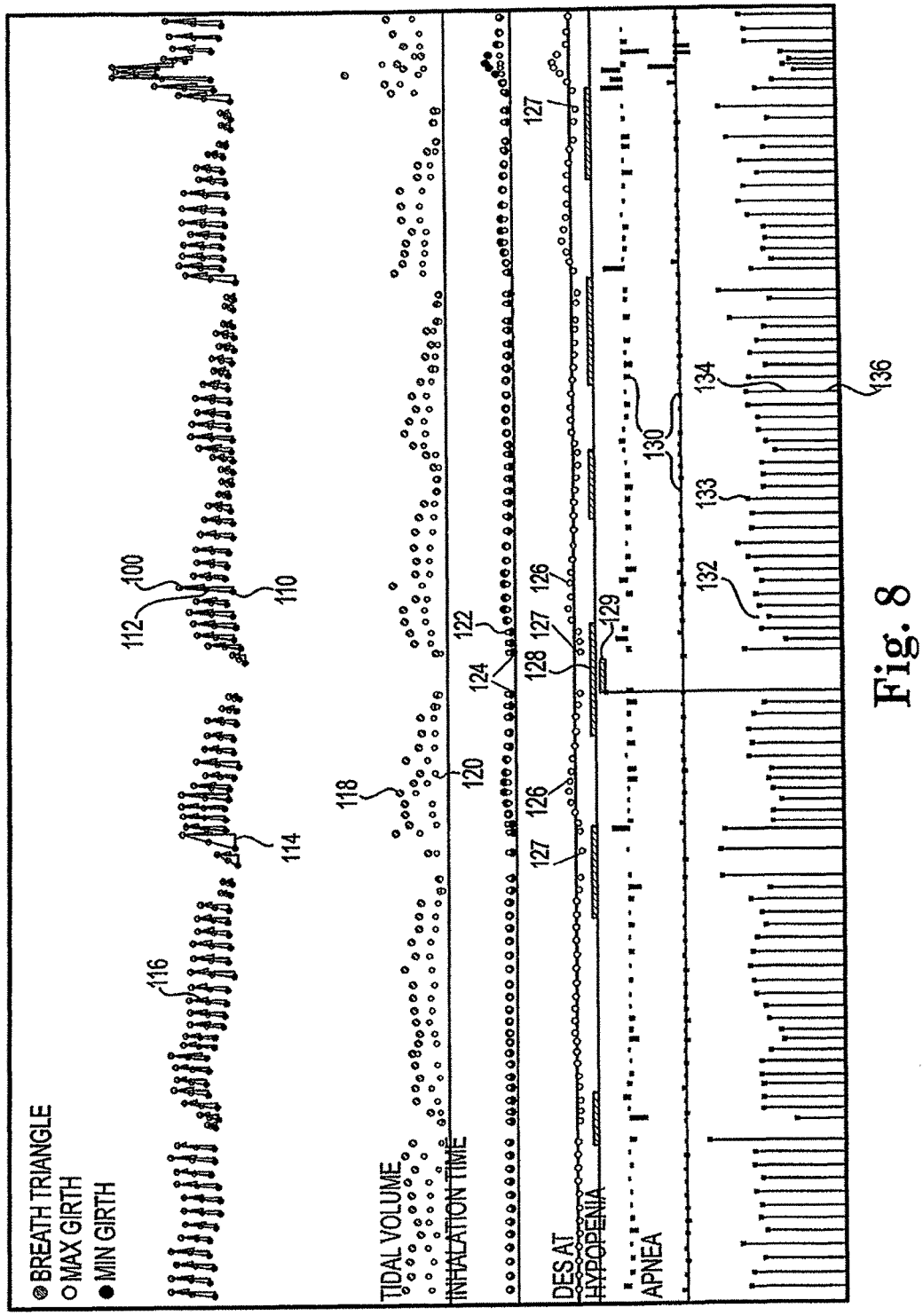
FIG. 8 is a graphic that illustrates the readout on a display of the data collected and processed by the system in accordance with the invention.

Referring now to FIG. 8 a graphic illustrates the visual display produced by the software and system in accordance with the invention for Cheyne Stokes syndrome. The maximum girth of a single breath is represented by 100. The minimum girth of a single breath is represented by 110 and the average girth of the breath is 112. The large triangle 114 represent another way to interpret a breath, the slope being the inhalation rate, the width being the inhalation time and the height being the Tidal Volume. Reference numeral 118 represents the Tidal Volume of a breath plotted against a base reference line. Reference numeral 120 denotes Fev1. A semaphore block is denoted by 122, 124. Reference numeral 122 is normalized Minute Volume looking at the last 20 breaths (used in this case as a reference Minute Volume which allows the microprocessor to calculate hypopnea drop). Reference numeral 124 is normalized Minute Volume of last four breaths (used to inspect 10 second groupings). Reference numeral 126 is a desaturation line showing dots representing MV4/MV20. As the dots dip below 1:1 the visual graphic shows a dot that is more "blue" 127 (blue color not shown) indicating or representing blood oxygen desaturation used to calculate hypopnea drop by the microprocessor or remote computer.

Reference numeral 128 indicates a hypopnea event or a period of ten seconds or more in which the MV4/MV20 drops thirty percent or more. MV4 refers to the last four breath's normalized Minute Volume cluster being tested. MV20 refers to the last twenty breath's normalized Minute Volume as reference. Reference numeral 129 indicates an apnea event or the total absence of breathing for ten seconds or more.

The next two lines of data in FIG. 8 indicated by 130 shows the jumps from breath to breath of the maximum girth data 100 and the minimum girth data 110 which is indicative of irregular breathing and gasp breaths. Lastly, the vertical line grouping of data 132 at the bottom of the graphic indicate the total breath cycle time 133 (upper dot), the exhalation time 134 and inhalation time 136.

As will further be appreciated by those skilled in the art, the processes previously described may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to as a "circuit," "module" or "system." Furthermore, the present invention may take the form of a computer program product embodied in any tangible medium of expression having computer usable program code embodied in the medium.

The processes comprising the method of the present invention have been described with reference to flow diagrams illustrating exemplary steps. It will be understood that each block of the flowchart diagrams, and combinations of blocks in the flowchart diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart diagram block or blocks.

The elastomeric strap in accordance with the invention wrapped once around the body, above or below the clothing configuration, i.e. against the skin or over clothing, is a good compromise between ease of use and reliability of Vte measurements in the context of sleep testing. It has been demonstrated that this once-around topology will underestimate extreme diaphragmatic breathing or other types of breathing disorders such as neck or upper chest shallow breathing. Other topologies of strap encirclement of the human body have been tested and calibrated revealing increased sensitivity to extreme breathing situation. Of note is the quad-wrap topology, easily integrated into an undershirt. Essentially the technology in accordance with the invention is able to approximate underlying volumetric changes in anything it is wrapped around, and the number of wraps increases the quality of this approximation.

Although the present invention has been described with reference to exemplary embodiments of the invention, those of ordinary skill in the art will recognize that changes may be made in form and detail without departing from the spirit and scope of the invention.

I claim:

1. A method for monitoring tidal volume of an individual to diagnose a condition comprising:
    providing a microprocessor component and an electrically-conductive, elastomeric band in electrical communication with the microprocessor component:
        wherein the microprocessor component comprises memory and a circuit for detecting postural orientation;
        wherein the electrically-conductive, elastomeric band comprises:
            an elasticity allowing a fifty percent change in elongation of the electrically-conductive, elastomeric band;
            a resistance that is linearly variable over a three to fifty percent change in elongation of the electrically-conductive, elastomeric band; and
            a first end and a second end;
        wherein the electrically-conductive, elastomeric band is physically connected with the microprocessor component in such a manner that, in conjunction with the elasticity of the electrically-conductive, elastomeric band, the microprocessor component and the first and second ends of the electrically-conductive, elastomeric band are maintained generally around the bottom of the individual's sternum and the electrically-conductive, elastomeric band extends and is maintained around the individual's thorax in a non-horizontal path that is higher at a front of the individual and lower along a back of the individual; and
        wherein, when so positioned, changes in measured resistance of the electrically-conductive, elastomeric band correspond to tidal volume of the individual;
    with the electrically-conductive, elastomeric band and the microprocessor component, monitoring respiratory activity of the individual during a period of time by causing said microprocessor component to collect raw resistance data from the electrically-conductive, elastomeric band a predetermined number of sample times per second;
    blurring the raw resistance data by averaging a given raw resistance data sample with raw resistance data over an immediately preceding 0.3 to 1.0 seconds of the raw resistance data to filter out artifacts;
    determining a beginning of a breath cycle and an end of a breath cycle based on the blurred data; and
    recording an adverse event if a pre-determined period of time has elapsed without a new breath cycle commencing.

2. The method of claim 1 wherein the electrically-conductive, elastomeric band comprises knitted, silver-coated nylon yarn.

3. The method of claim 1 wherein blurring the raw resistance data by averaging a given raw resistance data sample with raw resistance data over an immediately preceding 0.3 to 1.0 seconds of the raw resistance data to filter out artifacts comprises blurring the raw resistance data by averaging a given raw resistance data sample with raw resistance data over an immediately preceding 0.45 to 0.72 seconds of the raw resistance data.

4. The method of claim 3 wherein the artifacts include bodily movement and heartbeat noise.

5. The method of claim 1 wherein recording said adverse event comprises recording an apnea event, a hypopnea event or Cheyne Stokes syndrome.

6. The method of claim 1 further comprising monitoring whether one second has elapsed from commencement of exhalation by the individual but before inhalation by the individual commences, and if so, recording forced evacuation volume.

7. The method of claim 1, wherein the microprocessor component is connected between the first and second ends of the electrically-conductive, elastomeric band.

8. The method of claim 7, wherein the circuit for detecting postural orientation comprises an accelerometer.

9. A system for monitoring tidal volume of an individual to diagnose a condition comprising:
an electrically-conductive, elastomeric band having:
an elasticity allowing a fifty percent change in elongation of the electrically-conductive, elastomeric band;
a resistance that is linearly variable over a three to fifty percent change in elongation of the electrically-conductive, elastomeric band; and
a first end and a second end; and
a microprocessor component having memory and a circuit for detecting postural orientation, said microprocessor in electrical communication with the electrically-conductive, elastomeric band and having functionality in conjunction with the electrically-conductive, elastomeric band to:
monitor respiratory activity of the individual during a period of time;
collect raw resistance data from the electrically-conductive, elastomeric band a predetermined number of sample times per second;
blur the raw resistance data by averaging a given raw resistance data sample with raw resistance data over an immediately preceding 0.3 seconds to 1.0 seconds of the raw resistance data to filter out artifacts;
determine a beginning of a breath cycle and an end of a breath cycle based on the blurred data; and
record an adverse event if a pre-determined period of time has elapsed without a new breath cycle commencing;
wherein the electrically-conductive, elastomeric band is physically connected with the microprocessor component in such a manner that, in conjunction with the elasticity of the electrically-conductive, elastomeric band, the microprocessor component and the first and second ends of the electrically-conductive, elastomeric band are maintained generally around the bottom of the individual's sternum and the electrically-conductive, elastomeric band extends and is maintained around the individual's thorax in a non-horizontal path that is higher at a front of the individual and lower along a back of the individual.

10. The system of claim 9 wherein the electrically-conductive, elastomeric band comprises knitted silver coated nylon yarn.

11. The system of claim 9 wherein averaging a given raw resistance data sample with raw resistance data over an immediately preceding 0.3 to 1.0 seconds of the raw resistance data to filter out artifacts comprises averaging a given raw resistance data sample with raw resistance data over an immediately preceding 0.45 to 0.72 seconds of the raw resistance data.

12. The system of claim 9 wherein the artifacts include bodily movement and heartbeat noise.

13. The system of claim 9 wherein said adverse event comprises an apnea event, a hypopnea event or Cheyne Stokes syndrome.

14. The system of claim 9, wherein the microprocessor component is connected between the first and second ends of the electrically-conductive, elastomeric band.

15. The system of claim 14, wherein the circuit for detecting postural orientation comprises an accelerometer.

16. A method for monitoring tidal volume of an individual to diagnose a condition comprising:
providing an electrically-conductive, elastomeric band in communication with a microprocessor component having memory and a circuit for detecting postural orientation, the electrically-conductive, elastomeric band having an elasticity allowing a fifty percent change in elongation of the electrically-conductive, elastomeric band and a resistance that is linearly variable over a three to fifty percent change in elongation of the electrically-conductive, elastomeric band, the electrically-conductive, elastomeric band being physically connected with the microprocessor component in such a manner that, in conjunction with the elasticity of the electrically-conductive, elastomeric band, the microprocessor component is maintained generally around the bottom of the individual's sternum and the electrically-conductive, elastomeric band extends and is maintained around the individual's thorax in a non-horizontal path that is higher at a front of the individual and lower along a back of the individual and at least a portion of the electrically-conductive, elastomeric band falls in a path just above the lowest rib of the lower ribcage, wherein, when so positioned, changes in measured resistance of the electrically-conductive, elastomeric band correspond directly to tidal volume of the individual;
with the electrically-conductive, elastomeric band and the microprocessor component, monitoring respiratory activity of the individual during a period of time by causing said microprocessor component to collect raw resistance data from the electrically-conductive, elastomeric band a predetermined number of sample times per second;
blurring the raw resistance data by averaging a given raw resistance data sample with raw resistance data over an immediately preceding 0.3 to 1.0 seconds of the raw resistance data to filter out artifacts;
determining a beginning of a breath cycle and an end of a breath cycle based on the blurred data; and
recording an adverse event if a pre-determined period of time has elapsed without a new breath cycle commencing.

17. The method of claim 16 wherein blurring the raw resistance data by averaging a given raw resistance data sample with raw resistance data over an immediately preceding 0.3 to 1.0 seconds of the raw resistance data to filter out artifacts comprises blurring the raw resistance data by averaging a given raw resistance data sample with raw resistance data over an immediately preceding 0.45 to 0.72 seconds of the raw resistance data.

* * * * *